US012343023B2

(12) United States Patent
Siccardi et al.

(10) Patent No.: US 12,343,023 B2
(45) Date of Patent: Jul. 1, 2025

(54) CUTTING GUIDE FOR SPINAL OSTEOTOMY

(71) Applicant: MEDACTA INTERNATIONAL SA, Castel San Pietro (CH)

(72) Inventors: Francesco Siccardi, Castel San Pietro (CH); Meinrad Fiechter, Castel San Pietro (CH); Yuri Insinna, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 343 days.

(21) Appl. No.: 18/022,675

(22) PCT Filed: Aug. 17, 2021

(86) PCT No.: PCT/IB2021/057547
§ 371 (c)(1),
(2) Date: Feb. 22, 2023

(87) PCT Pub. No.: WO2022/049435
PCT Pub. Date: Mar. 10, 2022

(65) Prior Publication Data
US 2023/0301668 A1    Sep. 28, 2023

(30) Foreign Application Priority Data
Sep. 1, 2020  (IT) .................. 102020000020794

(51) Int. Cl.
*A61B 17/17*  (2006.01)
*A61B 17/56*  (2006.01)

(52) U.S. Cl.
CPC .... *A61B 17/1757* (2013.01); *A61B 2017/568* (2013.01)

(58) Field of Classification Search
CPC .................................................. A61B 17/1757
See application file for complete search history.

(56) References Cited

U.S. PATENT DOCUMENTS

| 10,016,241 B2 * | 7/2018 | Dupuis | G16B 5/00 |
| 2016/0030067 A1 * | 2/2016 | Frey | A61B 50/33 606/86 A |

(Continued)

FOREIGN PATENT DOCUMENTS

| EP | 2749235 A1 | 7/2014 |
| EP | 3466350 A1 | 4/2019 |
| WO | 2020170021 A1 | 8/2020 |

OTHER PUBLICATIONS

International Search Report and Written Opinion issued in PCT/IB2021/057547, mailed Dec. 23, 2021, 13 pages.

*Primary Examiner* — Christian A Sevilla
(74) *Attorney, Agent, or Firm* — Meunier Carlin & Curfman LLC

(57) ABSTRACT

A cutting guide for spinal osteotomy comprises two polyhedral blocks, each polyhedral block comprising a respective tubular guide member, each tubular guide member extends from a proximal opening to a distal opening and has an axial cavity extending along a longitudinal axis; a connecting bridge which connects the two polyhedral blocks to each other and is adapted to surmount a spinous process of said vertebra; and contact members designed to match a corresponding plurality of points of contact on the patient's vertebra to define a unique coupling configuration of the cutting guide on the patient's vertebra. The two polyhedral blocks each comprise at least a first and a second slotted body, associated in pairs with a respective tubular guide member, arranged one opposite the other with respect to the corresponding tubular guide member associated therewith.

9 Claims, 6 Drawing Sheets

(56) References Cited

U.S. PATENT DOCUMENTS

2017/0135706 A1* 5/2017 Frey .................. A61B 17/1671
2017/0135733 A1* 5/2017 Donner ............. A61B 17/7049
2019/0083271 A1* 3/2019 Donner ............. A61B 17/1739

* cited by examiner

CUTTING GUIDE FOR SPINAL OSTEOTOMY

FIELD OF APPLICATION

The present invention relates to a cutting guide for spinal osteotomy.

In the case of spinal deformities such as hyperkyphosis, lordosis or degenerative diseases, there is an unnatural curvature of the patient's spine. Therefore, there is no inter-disc space, with consequent deformation of the patient's posture and compression of the spinal cord.

When it is necessary to intervene to straighten the spine, a portion of the vertebral column needs to be removed and the vertebrae forced to take a correct anatomical shape. A commonly used technique is pedicle subtraction osteotomy (PSO), which allows obtaining excellent corrections of the deformity associated with a clinical and radiological improvement.

This procedure is used to fix kyphotic segments. A wedge-shaped incision is made to remove a triangle of bone, having its vertex facing anteriorly with respect to the patient's body, so that the vertebrae can be bent rearwards and brought closer to come into contact posteriorly.

Such a technique is particularly powerful, especially in the lumbar spine where the vertebrae are larger, and small corrections can lead to large improvements in posture.

PRIOR ART

The surgery usually consists in cutting a wedge-shaped portion of the vertebra to create a space which allows the vertebral column to be straightened.

Stiffening bars are then positioned and fixed with appropriate screws.

The cuts for osteotomy are currently made freehand without the aid of tools to guide the cutting blade; as a result, the cuts may be inaccurate, even though they may be planned on x-ray or CT scan before the surgery. A further difficulty of the current surgical technique consists in identifying the correct incision depth of the cut which must arrive in the vicinity of the medullary canal. Therefore, the vertebral bone structure is not completely severed but the last portion of the bone is broken manually.

This is to avoid also affecting the medullary canal with a complete cut, with consequent damage to the patient.

The front part of the vertebra(e) is removed by hand, taking as a reference the planes created with the removal of the rear part.

Moreover, a further complication of the current surgical technique is the inclination of the cutting planes, which are not always easy to identify intra-operatively.

In fact, there are no navigation systems for performing osteotomies on the vertebral column which give the surgeon a precise and sure reference of the incision line and depth.

Upon the osteotomy, the vertebral column needs to be realigned, which procedure requires the stabilization of the vertebrae not affected by the osteotomy, in the new desired shape by means of stiffening bars fixed to the vertebrae through pedicle screws.

It is the object of the present invention to overcome the drawbacks of the prior art.

In particular, it is the object of the present invention to suggest a cutting guide for spinal osteotomy which is specific for the patient.

It is a further object of the present invention to provide a cutting guide for spinal osteotomy which exactly identifies the planes along which the surgeon must cut the vertebrae, thus facilitating the surgery itself as well as ensuring greater safety for the patient.

It is another object of the present invention to provide a cutting guide for spinal osteotomy which is capable of defining a pre-defined cutting depth which ensures the exact incision depth, avoiding the risk of damage to the medullary canal.

Furthermore, last but not least, an object of the present invention to provide a cutting guide which allows it to be fixed to the vertebra itself by means of screws, so as to allow the surgeon to make a precise and safe cut of the vertebra portion to be removed.

These and further objects and advantages are achieved by a cutting guide for spinal osteotomy as disclosed in the appended claims.

SUMMARY

A first aspect of the present invention includes a cutting guide for spinal osteotomy which comprises two polyhedral blocks, each comprising a respective tubular guide member.

Each tubular guide member extends from a proximal opening to a distal opening and has an axial cavity, to guide the insertion of a surgical instrument on a patient's vertebra, extending along a longitudinal axis. A connecting bridge, which connects said two polyhedral blocks to each other, is adapted to surmount a spinous process of the vertebra. The guide further comprises contact members designed to match a corresponding plurality of surfaces or points of contact on the patient's vertebra, in order to define a unique coupling configuration of the cutting guide on the patient's vertebra. The polyhedral blocks each comprise at least a first and a second slotted body, associated in pairs with a respective tubular guide member, arranged one opposite the other with respect to the corresponding tubular guide member associated therewith. The first and second slotted bodies have respective extension surfaces, which define the cutting planes, converging below the proximal opening of the respective tubular guide member.

The first and second slotted bodies are arranged about the respective tubular guide member, in the caudal and cranial position, respectively, considering the cutting guide in a position of coupling with the corresponding vertebra.

The guide further comprises a third and a fourth slotted body, associated in pairs with a respective tubular guide member; the third slotted body is arranged opposite the fourth slotted body, with respect to the corresponding tubular guide member associated therewith. Advantageously, the third and fourth slotted bodies are arranged on the sides of the first and second slotted bodies of each tubular guide member, respectively, so that each tubular guide member is associated with the four slotted bodies. Preferably, the third and fourth slotted members are interposed between the first and second slotted bodies.

The third and fourth slotted bodies also have respective extension surfaces, which define cutting planes. The extension surfaces are transverse to the extension surfaces of the first and second slotted bodies. The extension surfaces of all the slotted bodies are planned by the surgeon and the inclination thereof is determined in the preoperative step according to the patient's anatomy and the vertebra to be dissected.

The inclination of the extension surfaces, defining the cutting planes, of the slotted bodies may vary about a longitudinal and/or sagittal axis of the patient.

In some surgical situations, the third and/or fourth slotted bodies may be communicating with the first or second slotted body, to define a continuous U-shaped slot.

Advantageously, the connecting bridge comprises pre-weakening lines close to the area of connection with the tubular guide members and a breaking tool to cause the breakage and removal of the bridge itself, so that the surgeon has better visibility of the central area of the vertebra.

The connecting bridge also has a lower surface shaped according to the patient's anatomy, so as to rest on the spinous process of the vertebra in a unique and stable manner.

The connecting bridge further comprises a handle, preferably placed above the area surmounting the spinous process, in order to keep the guide in place and facilitate the removal of the bridge part separated from the rest of the guide upon the breakage.

BRIEF DESCRIPTION OF THE DRAWINGS

The present invention will become clearer from the following detailed description, with reference to the accompanying drawings merely provided by way of example, in which.

DETAILED DESCRIPTION

Figure 1:
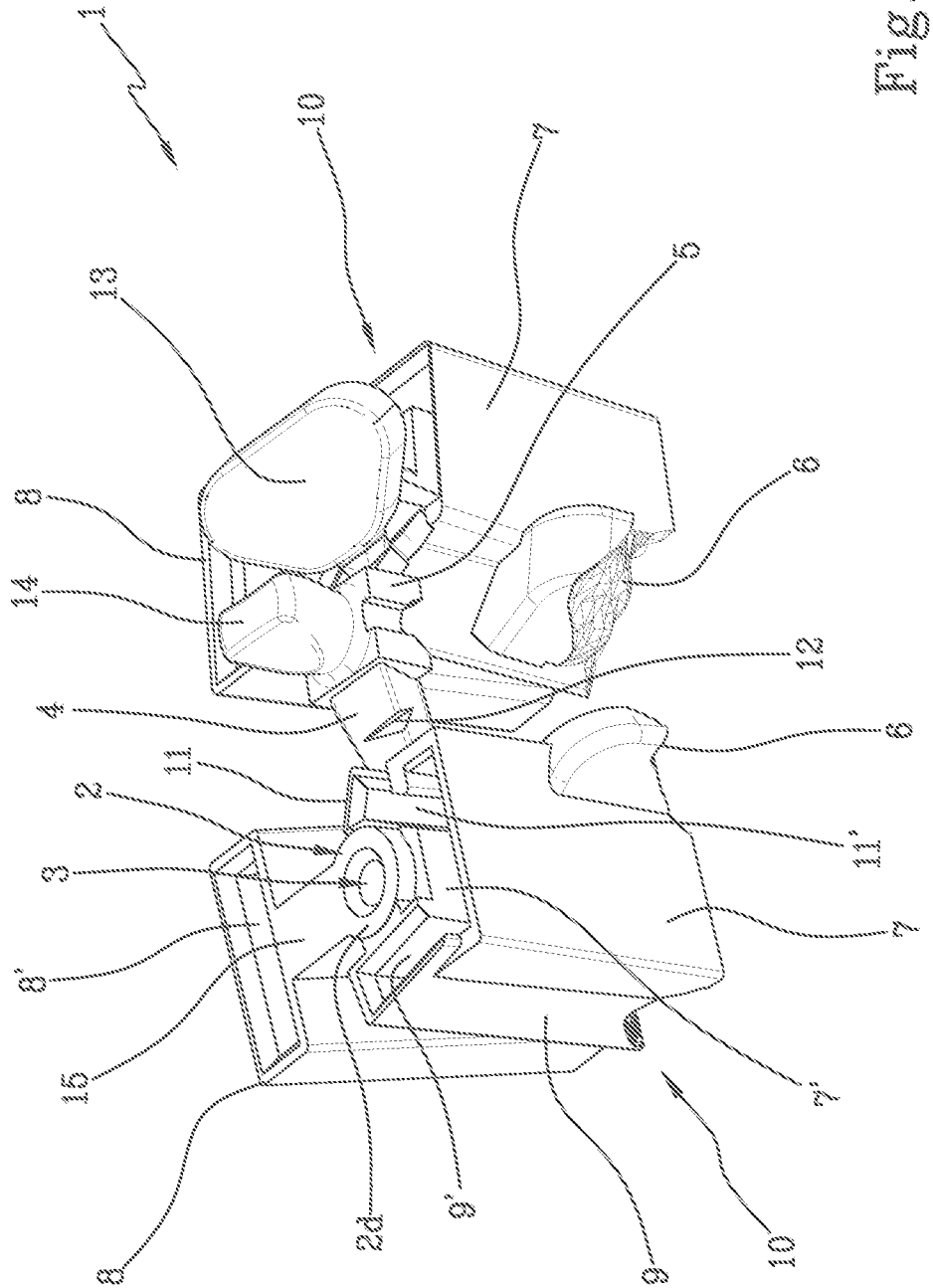
FIG. 1 shows a perspective view, from the caudal side, of a cutting guide for spinal osteotomy according to the present invention.
Figure 2:
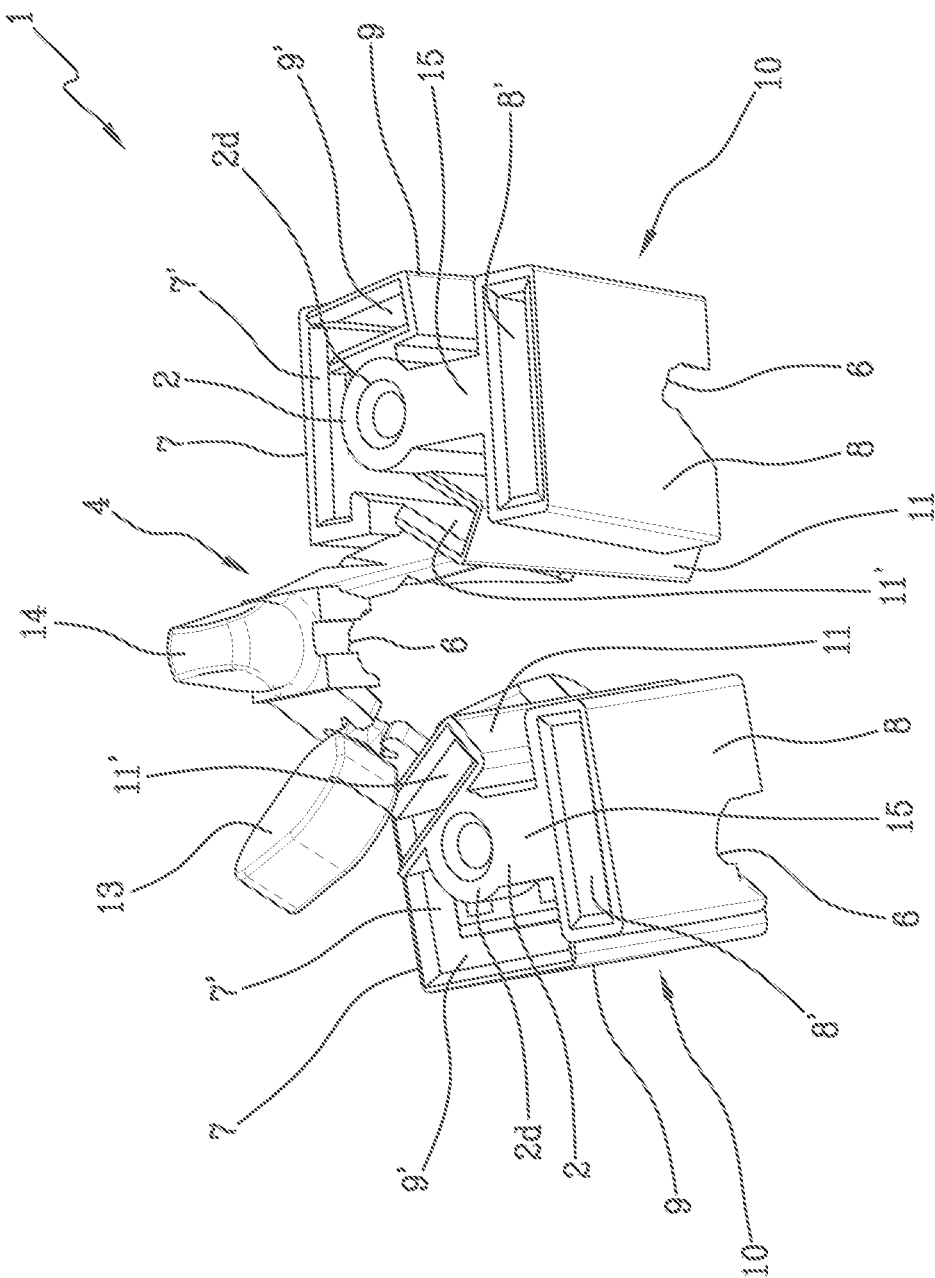
FIG. 2 shows a perspective view, from the cranial side, of the cutting guide for spinal osteotomy according to the present invention.
Figure 3:
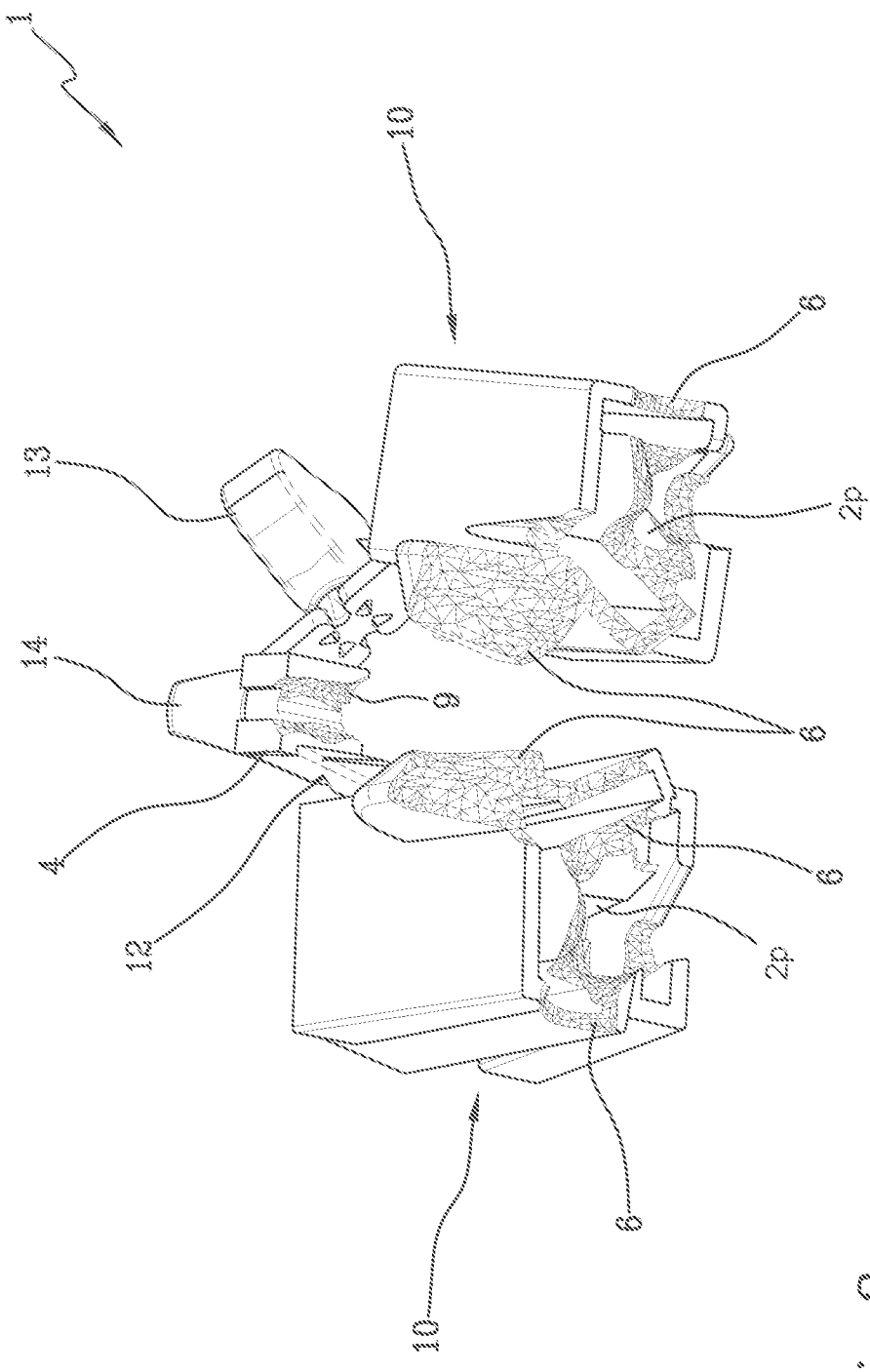
FIG. 3 shows a lower perspective view of the cutting guide according to the present invention.

In the aforementioned drawings, reference numeral 1 generally indicates a cutting guide for spinal osteotomy in accordance with the present invention.

The cutting guide 1, described below, is used to perform cuts according to cutting plans planned before the surgery, in accordance with the specifications provided by the surgeon, on a specific vertebra 100 or fusion of two or more vertebrae. Such a guide 1 thus serves to make incisions, preferably wedge-shaped, on one or more vertebrae, after which it is possible to remove even significant portions of vertebrae or parts of vertebrae, in order to proceed with straightening the vertebral column.

The cutting guide 1 of the present invention is also a navigation guide which allows precisely guiding surgical instruments, such as drill bits, pedicle screws or Kirchner wires, directly on the vertebra, in a precise selected point, so as to make a pre-hole or to implant the screws which will be used to fix the cutting guide to the vertebra, for example, in order to reduce possible movements of the guide itself during the cutting operations.

More specifically, the cutting guide 1 comprises two polyhedral blocks 10, each of which comprises a respective tubular guide member 2.

Therefore, the cutting guide 1 comprises two tubular guide members 2, adapted to guide the insertion of a respective surgical instrument, such as drill bits, pedicle screws or Kirchner wires, on a patient's vertebra 100. Each tubular guide member 2 has an axial cavity 3, extending along a longitudinal axis 2a, to guide the insertion of the aforementioned surgical instruments up to the vertebra 100. Furthermore, each tubular guide member 2 extends from a proximal opening 2p, adapted to face the vertebra 100, to a distal opening 2d, opposite the proximal opening 2p, and facing upwards when the guide is in use, associated with a patient's vertebrae.

The proximal opening 2p and the distal opening 2d are placed at the ends of the axial cavity 3.

Therefore, the term "proximal" means the part closest to the patient's body, while the term "distal" refers to the part farthest from the patient's body, considering the guide in a configuration of use, associated with the patient's vertebra 100.

As can be seen in the accompanying drawings, the cutting guide 1 further comprises a connecting bridge 4, which connects the two polyhedral blocks 10 to each other and therefore, as a result, the tubular guide members 2. The bridge 4 is adapted to surmount a spinous process 101 of the vertebra 100.

Preferably, the bridge has an apex 5 which, in the configuration of use, is adapted to position and abut just above the spinous process of the vertebra.

The cutting guide 1 is provided with a plurality of contact members 6 designed to match with a corresponding plurality of surfaces or points of contact on the patient's vertebra 100, in order to define a unique coupling configuration of the cutting guide 1 on the patient's vertebra. Such contact members 6 are arranged below the two polyhedral blocks 10, or projecting like a finger from the latter (as can be seen in FIG. 1, for example) and below the connecting bridge 4, in particular below the apex 5 of the connecting bridge 4.

Specifically, the contact members, both those located below the polyhedral blocks 10 and those located below the bridge, thus the lower surface of the bridge, including the apex, are shaped according to the patient's anatomy so as to rest on the vertebra in a unique and stable manner.

The polyhedral blocks 10 each comprise at least a first 7 and a second 8 slotted body, associated in pairs with a respective tubular guide member 2. The first 7 and second 8 slotted bodies are opposite each other with respect to the corresponding tubular guide member 2 associated therewith.

In particular, the first 7 and second 8 slotted bodies are arranged about the respective tubular guide member 2 in the caudal and cranial position, respectively, considering the cutting guide 1 in a position of coupling with the vertebra 100. The guide 1 associated with a vertebra can be seen in FIG. 4: the front part seen in FIG. 4 is the caudal area, while the opposite part, not seen, is the cranial one.

Figure 4:
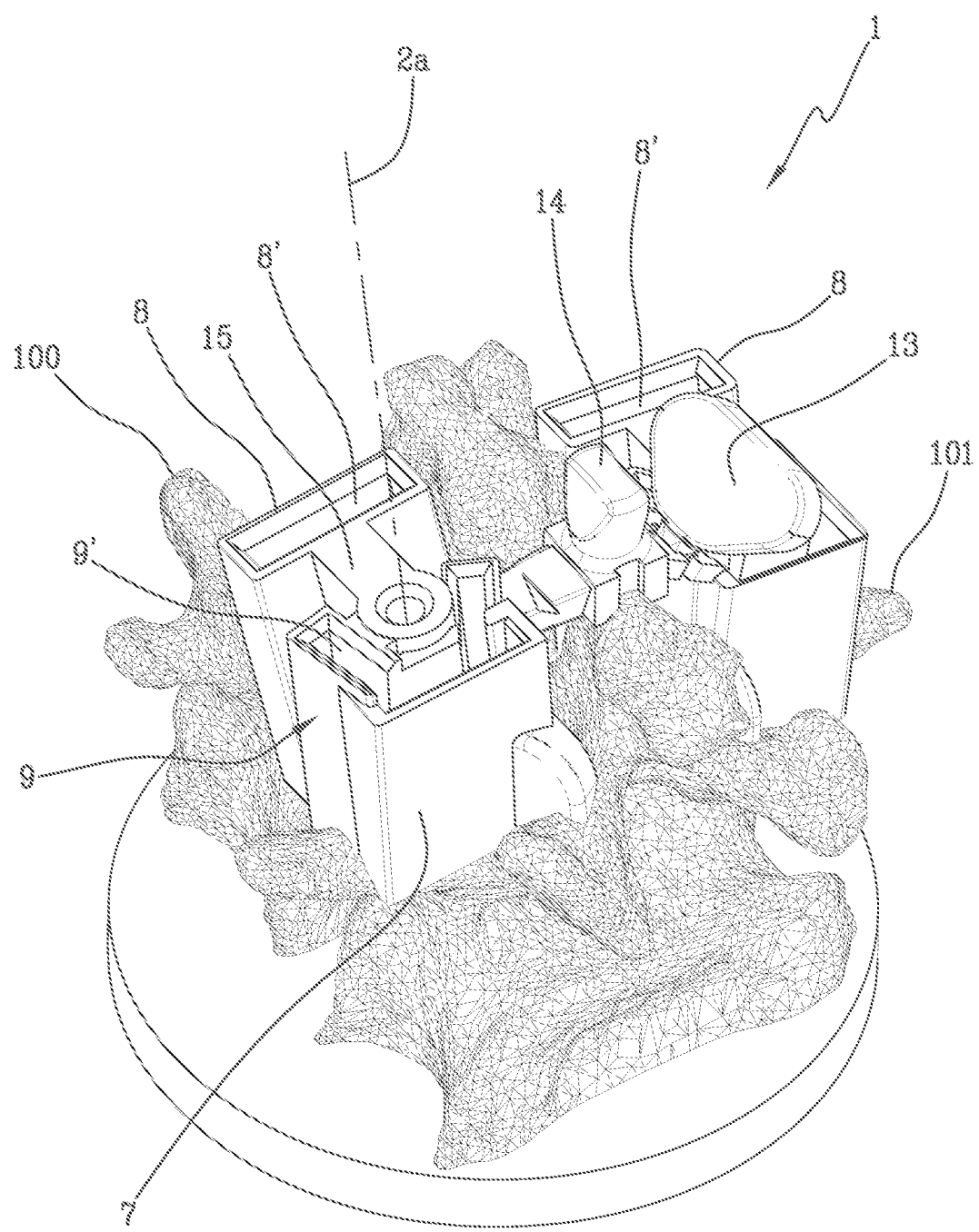
FIG. 4 shows a perspective view, from the caudal side, of the cutting guide for spinal osteotomy according to the present invention associated with a vertebra.
Figure 5:
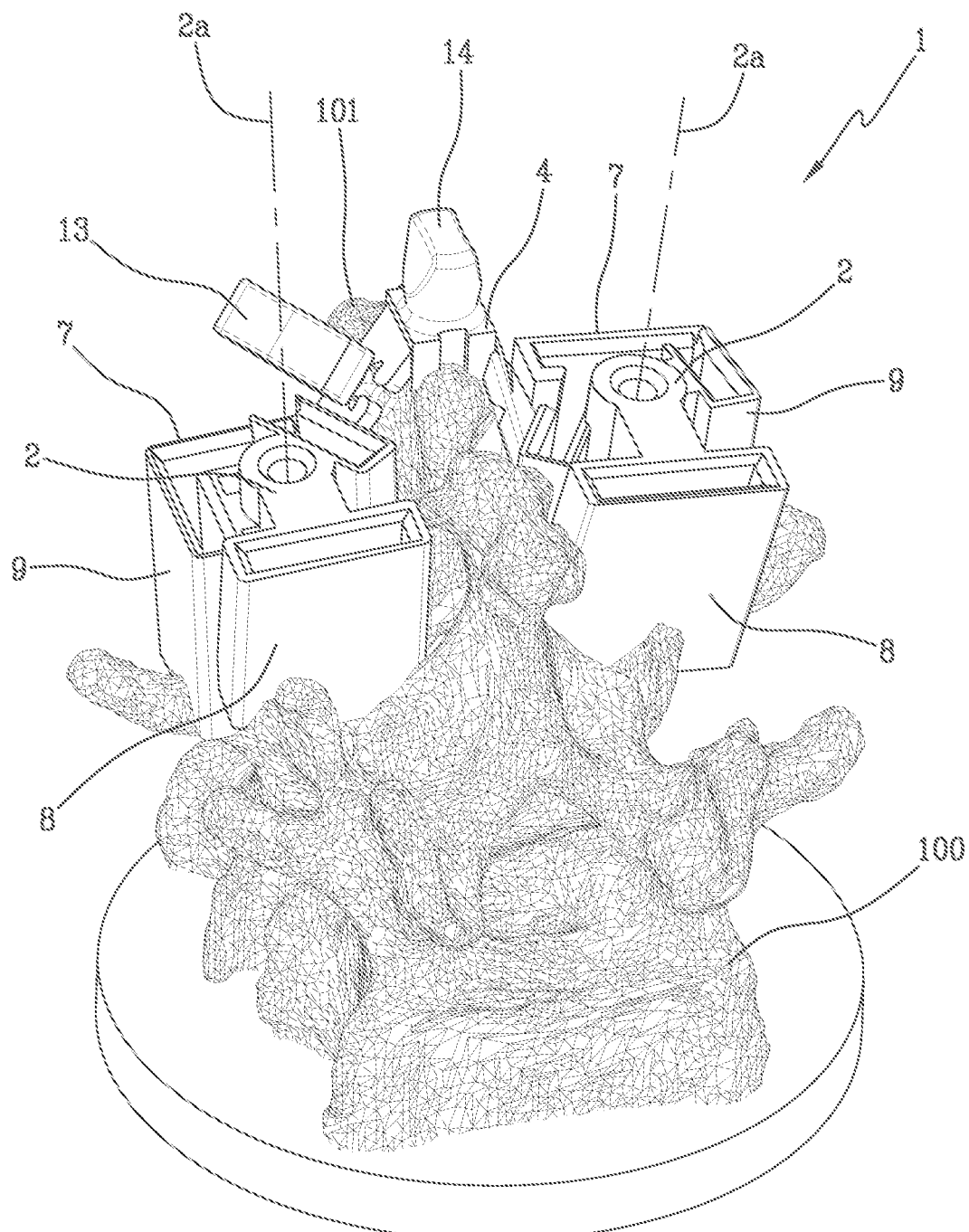
FIG. 5 shows a perspective view, from the cranial side, of the cutting guide for spinal osteotomy according to the present invention associated with a vertebra.
Figure 6:
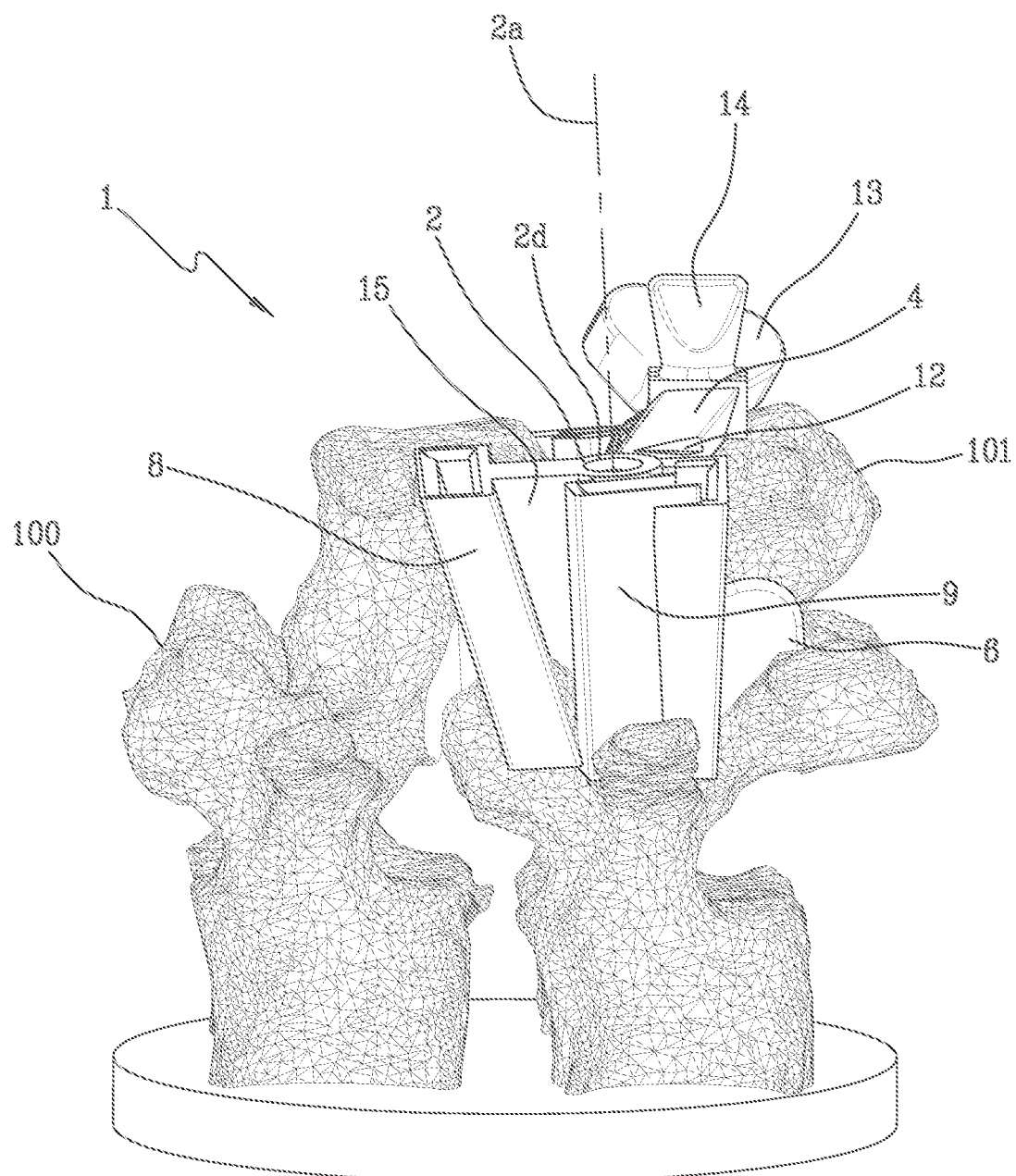
FIG. 6 shows a side view of the cutting guide, according to the present invention, associated with a vertebra.

The same guide associated with the same vertebra in FIG. 4 is also shown in FIG. 5, but oriented in the opposite direction: the front part seen in FIG. 5 is the cranial area, while the opposite part, not seen, is the caudal one.

As can be clearly seen in the accompanying drawings, the first 7 and second 8 slotted bodies have respective extension surfaces 7' and 8', which define the cutting planes, converging below the proximal opening 2p of the respective tubular guide member 2.

The polyhedral blocks 10 further comprise a third 9 and a fourth 11 slotted body, associated in pairs with a respective tubular guide member 2. These third 9 and fourth 11 slotted bodies are opposite each other with respect to the corresponding tubular guide member 2 associated therewith, and arranged on the sides of the first 7 and second 8 slotted bodies, respectively. As can be seen in the accompanying drawings, the third 9 and fourth 11 slotted bodies are placed between the first 7 and second 8 slotted bodies. Specifically, the third 9 and fourth 11 slotted bodies have respective extension surfaces 9' and 11', which define the cutting planes, arranged transversely to the extension surfaces of the first 7 and second 8 slotted bodies.

The third 9 and fourth 11 slotted bodies abut on the transverse process and the lamina, respectively, which should be cut.

The four slotted bodies are connected to the respective tubular guide members directly or by means of connecting structures 15

The extension surfaces of the slotted bodies, thus not only of the first 7 and second 8 slotted bodies, but also those of the third 9 and fourth 11 slotted bodies, are planned by the surgeon, and the inclination thereof is determined in the preoperative step according to the patient's anatomy and the vertebra portion to be dissected.

The inclination of the extension surfaces 9', 11' defining the cutting planes of the third 9 and fourth 11 slotted bodies may vary about a longitudinal and/or sagittal axis of the patient.

The four slotted bodies may not be communicating with one another, thus the slots defining the cutting surfaces may be separated from one another or, as shown incidentally in the accompanying drawings which are merely given by way of non-limiting example, may be mutually communicating. Therefore, the third 9 and/or fourth 11 slotted bodies may be communicating with the first 7 or second 8 slotted body to define a continuous U-shaped slot.

As can be seen in FIGS. 1 and 4, the connecting bridge 4 comprises pre-weakening lines 12 and a breaking tool 13 to cause the breakage and removal of the bridge itself, so that the surgeon may have, once the guide is positioned and fixed on the vertebra, better visibility of the central area of the vertebra.

The connecting bridge 4 further comprises a handle 14, placed above the area surmounting the spinous process, thus above the apex 5, in order to keep the guide in a stable position, during the first steps of positioning and connecting the guide to the vertebra, and to remove the part of the bridge upon the breakage to leave the central area of the vertebra free.

In use, the cutting guide 1 is used to perform resections of the following vertebral parts: transverse process, lamina, and vertebral body.

The cutting guide is positioned on the vertebra to be dissected and stabilized by means of the contact members shaped according to the specific patient's anatomy. Holes are then drilled with a surgical instrument through the tubular guide members and screws are then placed to fix the guide to the vertebra.

The transverse processes and the laminae are then resected through the appropriate housings defined by the third 9 and fourth 11 slotted bodies. After this step, the central part of the guide, specifically the connecting bridge 4, may be separated from the polyhedral blocks 10, by rotating the breaking tool 13 and leveraging the pre-weakening lines 12, and then removed so as to have a better visibility of the central area of the vertebra. Finally, the cranial and caudal housings, defined by the first 7 and second 8 slotted bodies, are used to resect the vertebral body.

The handle 14 allows keeping more easily the guide in place and leverage more easily during the breaking of the central part of the guide, i.e., of the bridge 4.

The main innovation is the possibility of performing vertebral resections by means of specific housings, thus of slotted bodies, according to the size of the instrument used.

The cutting planes of these resections are planned by the surgeon and are precisely represented by the slotted bodies, through which the cutting blades are inserted, for the resection of the vertebral parts.

The axial cavities present in the tubular guide members allow fixing the guide to the vertebra in order to reduce any movement of the guide itself when the cuts are made.

Furthermore, the possibility of removing the central part of the guide, using a breaking tool, helps the surgeon to have a wider view of the resection area.

The invention claimed is:

1. A cutting guide for spinal osteotomy, comprising two polyhedral blocks, each comprising a respective tubular guide member, each tubular guide member extending from a proximal opening to a distal opening and having an axial cavity, to guide the insertion of a surgical instrument on a patient's vertebra, extending along a longitudinal axis; a connecting bridge, which connects said two polyhedral blocks to each other, adapted to surmount a spinous process of said vertebra; and contact members designed to match a corresponding plurality of surfaces or points of contact on the patient's vertebra in order to define a unique coupling configuration of the cutting guide on the patient's vertebra; wherein said polyhedral blocks each comprise at least a first and a second slotted body, said first and second slotted body being associated in pairs with a respective tubular guide member and being arranged one opposite the other with respect to the corresponding tubular guide member associated therewith, said first and second slotted bodies having respective extension surfaces, which define cutting planes, converging below the proximal opening of the respective tubular guide member.

2. The cutting guide according to claim 1, wherein said first and second slotted bodies are arranged about the respective tubular guide member in caudal and cranial position, respectively, considering the cutting guide in a position of coupling with said vertebra.

3. The cutting guide according to claim 1, wherein said polyhedral blocks each comprise a third and a fourth slotted body, associated in pairs with a respective tubular guide member, arranged one opposite the other with respect to the corresponding tubular guide member associated therewith, and arranged on the sides of the first and second slotted bodies, respectively.

4. The cutting guide according to claim 3, wherein said third and fourth slotted bodies have respective extension surfaces, which define cutting planes of the third and fourth slotted bodies, transversal with respect to the extension surfaces of said first and second slotted bodies.

5. The cutting guide according to claim 4, wherein said extension surfaces and the inclination thereof are determined preoperatively according to the patient's anatomy and the vertebra to be dissected.

6. The cutting guide according to claim 3, wherein said third and/or fourth slotted bodies may communicate with said first or said second slotted body to define a continuous U-shaped slot.

7. The cutting guide according to claim 1, wherein said connecting bridge comprises pre-weakening lines and a breaking tool to cause the breakage and removal of the bridge itself.

8. The cutting guide according to claim 1, wherein said connecting bridge has a lower surface shaped according to the patient's anatomy so as to rest on the spinous process of said vertebra.

9. The cutting guide according to claim 1, wherein said connecting bridge comprises a handle configured to be placed above the area surmounting the spinous process in order to keep the guide in a stable position.

* * * * *